(12) United States Patent
Stout et al.

(10) Patent No.: US 7,377,952 B2
(45) Date of Patent: May 27, 2008

(54) SYSTEM AND METHOD FOR REMOVING CONTAMINATES FROM THE AIR IN A MAIL-SORTING ROOM

(75) Inventors: David A. Stout, Mountain Home, AR (US); William R. Lehman, Grady, AR (US)

(73) Assignee: American Safe Air, Inc., Mountain Home, AR (US)

( * ) Notice: Subject to any disclaimer, the term of this patent is extended or adjusted under 35 U.S.C. 154(b) by 2 days.

(21) Appl. No.: 11/216,083

(22) Filed: Sep. 1, 2005
(Under 37 CFR 1.47)

(65) Prior Publication Data
US 2007/0277484 A1    Dec. 6, 2007

Related U.S. Application Data

(63) Continuation of application No. 10/015,583, filed on Dec. 17, 2001, now Pat. No. 6,960,244.

(51) Int. Cl.
*A61L 2/00* (2006.01)
*A61L 2/14* (2006.01)
*F24F 9/00* (2006.01)
*F24F 13/06* (2006.01)

(52) U.S. Cl. .................. 55/385.2; 55/473; 55/DIG. 18; 55/DIG. 29; 55/DIG. 46; 454/187; 454/190; 454/236; 454/296; 379/350; 422/300; 436/48; 312/1

(58) Field of Classification Search ............... 55/385.2, 55/470, 473, DIG. 18, DIG. 29, DIG. 46; 454/187, 236, 56, 67, 344; 95/285, 287; 379/350; 422/300; 436/48; 312/1
See application file for complete search history.

(56) References Cited

U.S. PATENT DOCUMENTS

| | | | | | |
|---|---|---|---|---|---|
| 4,267,769 | A | * | 5/1981 | Davis et al. | 454/187 |
| 4,304,224 | A | * | 12/1981 | Fortney | 600/21 |
| 4,351,475 | A | * | 9/1982 | Hudson | 237/46 |
| 4,409,889 | A | * | 10/1983 | Burleson | 454/187 |
| 4,850,268 | A | * | 7/1989 | Saito et al. | 454/341 |
| 5,010,777 | A | * | 4/1991 | Yehl et al. | 73/864.81 |
| 5,064,457 | A | * | 11/1991 | Weber | 55/385.2 |
| 5,074,894 | A | * | 12/1991 | Nelson | 96/224 |
| 5,074,897 | A | * | 12/1991 | Sikich | 55/385.2 |
| 5,099,751 | A | * | 3/1992 | Newman et al. | 454/238 |
| 5,181,883 | A | * | 1/1993 | Hofstra et al. | 454/49 |
| 5,316,560 | A | * | 5/1994 | Krone-Schmidt et al. | 55/385.2 |

(Continued)

*Primary Examiner*—Duane Smith
*Assistant Examiner*—Minh-Chau T. Pham
(74) *Attorney, Agent, or Firm*—Miles & Stockbridge P.C.; David R. Schaffer, Esq.

(57) ABSTRACT

An air decontamination system including a sealed room to hold at least one person and the sealed room having an air inlet. The system further including a vacuum unit to create a negative pressure within the sealed room, by suctioning air through the air inlet into the sealed room and then from the sealed room into an inlet of the vacuum unit. The system still further including a work surface disposed in the sealed room at a predetermined height above a floor of the sealed room and the work surface to receive at least one mail piece and the air to be suctioned downwardly over the at least one mail piece and the work surface; and a filter unit to filter the air as the air is drawn out of the sealed room.

20 Claims, 3 Drawing Sheets

U.S. PATENT DOCUMENTS

| | | | |
|---|---|---|---|
| 5,326,316 A * | 7/1994 | Hashimoto et al. | 454/187 |
| 5,472,466 A * | 12/1995 | Oler | 55/385.2 |
| 5,558,112 A * | 9/1996 | Strieter | 134/103.2 |
| 5,626,820 A * | 5/1997 | Kinkead et al. | 422/122 |
| 6,010,400 A * | 1/2000 | Krainiak et al. | 454/187 |
| 6,692,348 B1 * | 2/2004 | Cauthorne | 454/230 |
| 6,737,029 B2 * | 5/2004 | Miller et al. | 422/300 |
| 6,777,355 B2 * | 8/2004 | Kisakibaru et al. | 438/800 |
| 6,811,587 B1 * | 11/2004 | Lorey et al. | 55/385.2 |
| 6,960,244 B2 * | 11/2005 | Lehman | 95/273 |
| 6,966,937 B2 * | 11/2005 | Yachi et al. | 55/385.2 |
| 7,134,444 B2 * | 11/2006 | Mintie et al. | 135/131 |
| 2003/0038564 A1 * | 2/2003 | Drinkwater | 312/1 |
| 2003/0101700 A1 * | 6/2003 | Burdine et al. | 55/385.2 |
| 2004/0221554 A1 * | 11/2004 | Iijima et al. | 55/385.2 |
| 2006/0107635 A1 * | 5/2006 | Homan et al. | 55/385.2 |

* cited by examiner

SYSTEM AND METHOD FOR REMOVING CONTAMINATES FROM THE AIR IN A MAIL-SORTING ROOM

CROSS REFERENCE TO RELATED APPLICATION

This application is a continuation application of U.S. patent application Ser. No. 10/015,583, filed Dec. 17, 2001, now U.S. Pat. No. 6,960,244 and claims the benefit of priority thereto".

BACKGROUND OF THE INVENTION

1. Field of the Invention

This invention generally relates to air filtration systems, and more particularly to a system and method for removing contaminates and other particulate matter from the air in a mail sorting room. The invention has particular application to reducing cross-contamination caused by a letter laced with anthrax or another harmful biological substance.

2. Description of the Related Art

Mail security has more than ever before become a vital national security interest. For the first time in our nation's history, the mail has been used as a vehicle of terrorism both by domestic and foreign enemies. The World Trade Center tragedy made every American painfully aware of the scope of destruction a determined terrorist could exact. This tragedy resulted in the loss of more than six thousand lives in the two most prominent cities of this nation, and is generally considered to be the defining event which marked a new age in terrorism.

While these cataclysmic acts have left their emotional mark on the American psyche to be sure, an evil far greater than suicide highjackers serves as the most serious threat today. This evil has the potential of operating as a silent killer and of taking far more lives than most wars. In fact, experts acknowledge that bioterrorism, if exacted in epidemic proportions, can result in a loss of life measurable in the tens or even hundreds of thousands.

In our most recent experiences with terrorism, what was once thought of as an unlikely threat became a grim reality. Letters addressed to prominent media figures and public officials were sent through the mail laced with anthrax. This resulted in infecting not only the staff of the intended recipients but also members of their families. Perhaps even more shockingly, many post office employees who carried and sorted the unopened letters also contracted and died from the disease.

In at least two cases, anthrax infection resulted from cross-contamination, a phenomenon which occurs, for example, when anthrax spores migrate from one letter to another letter or person. Authorities have determined that this could happen when the anthrax-contaminated letter comes into physical contact with another letter or when the spores become airborne and susceptible to inhalation.

A number of approaches have been proposed for dealing with anthrax exposure and other bio-terrorist acts perpetrated through the mail. One approach involves equipping mail sorting personnel with gloves and masks designed to protect against airborne particulates. This approach has often proven to be ineffective for protecting the facility. If small enough, anthrax spores will become suspended in the air for long periods of time. This makes them exceptionally difficult to protect against. For example, any patch of exposed skin could become infected even if gloves and a mask are worn. The spores could also attach themselves to the workers clothes, which could result in infecting anyone coming into contact with them.

Another approach involves irradiating the mail at some point prior to delivery. While this may prove to be effective in a certain percentage of cases, there is no guarantee that irradiation will kill all of the biological contaminates associated with a given letter. Irradiation does not solve the problem of contamination or cross-contamination resulting from airborne anthrax spores one-hundred percent of the time. Furthermore, security issues exist from the irradiation unit to the end-user or client.

In view of the foregoing considerations, it is clear that there is a critical need for an improved system and method of protecting mail-sorting personnel and facilities from biological contamination, and moreover one which is especially effective in preventing infection resulting from cross-contamination.

SUMMARY OF THE INVENTION

It is one object of the present invention to provide an improved system and method for protecting mail-sorting personnel from exposure to anthrax and other forms of deadly biological substances that have a tendency to become airborne during handling.

It is another object of the present invention to provide a system and method of the aforementioned type which is especially effective in protecting facilities and workers from infection resulting from cross-contamination effects.

It is another object of the present invention to provide a system and method of the aforementioned type which may be used by both the public and private sector.

It is another object of the present invention to provide a system of the aforementioned type which is transportable, easy to implement, and easy to adapt to any user's particular needs or space requirements.

It is another object of the present invention to provide a system and method of the aforementioned type which may be used in combination with other approaches to provide an integrated solution to decontaminating a mail sorting room.

It is another object of the present invention to provide a system and method of the aforementioned type which also protects personnel against chemical hazards during a mail sorting process.

The foregoing and other objects of the invention are achieved by a decontamination system which includes a sealed mail sorting room having an air inlet and an air outlet, a vacuum unit which creates a negative pressure within the mail sorting room, and a filter unit which filters air on its way out of the outlet of the mail sorting room. The vacuum unit creates negative pressure by suctioning air, first, through the air inlet and, then, from inside the sorting room into an inlet of the vacuum unit. The filter unit filters the air which is suctioned into the inlet of the vacuum unit.

The mail sorting room preferably has a modular construction with walls, a ceiling, and a floor which may all be removable. The walls may be transparent or opaque and one of them includes a door. If desired, the room may be constructed with multiple rooms, each of which may be used as a separate mail sorting area with a separate table. To prevent contaminates from escaping, an air lock room may be connected to the mail sorting room. The negative suction created in the mail sorting room draws air from an outside source into the air lock room, and then air from the lock room is then sucked into the mail sorting room. The air lock room, thus, serves as a buffer area. If desired, a filter unit may be used to filter the air before it is drawn into the air lock room. A door is included for allowing persons to pass from the air lock room to mail sorting room. The door is preferably self-sealing. The system may further include an intercom system and a warning device for informing outside personnel that a room is in use.

In operation, the vacuum unit creates a downwardly directed flow of air which passes from the air inlet into the mail sorting room. Once in the sorting room, the air enters the inlet of the vacuum unit, after which it is then filtered and expelled. For stability and consistency reasons, the air flow is preferably laminar in nature. The filter may have multiple stages, where in a first stage larger size particles are removed and in a second stage smaller sized particles are removed. A third filter may be used to remove chemical threats. The present invention is advantageous because it provides a work environment which protects personnel both inside and out of the room from exposure to contaminates.

The present invention is also a mail cleaning system suitable for use in the mail sorting room. This system includes a chamber, a vacuum unit, and a filter. The chamber has an air inlet and an air outlet and the vacuum unit is connected to the air outlet. The vacuum unit suctions air through the air inlet to create a high-velocity air flow through the chamber. Mail is then inserted into an entrance of the chamber by hand or by a conveyor. The high-velocity air flow removes contaminates from the mail, and the filter removes contaminates from the air flow.

DESCRIPTION OF THE PREFERRED EMBODIMENTS

The present invention is a system and method for removing contaminates from the air in a mail sorting room. The mail sorting room may be one which includes letters, packages, parcels, or any other type of container or object that may be sent through the mail or shipped by a carrier. The contaminates may be ones that are harmful or even deadly to human beings. Examples include anthrax spores, smallpox, botulism, salmonella and other types of pathogens, viruses, or bacteria. By removing these types of contaminates from the air, the invention will protect U.S. Postal Service workers and employees in private mail rooms exposure to bio-terrorist attacks, especially in the case where infection could occur as a result of cross-contamination.

The present invention may also be useful in removing airborne contaminates which are not particularly harmful to humans, but instead are merely considered to be a nuisance. Examples include dust and pollen which may produce an allergic or even asthmatic reaction in mail-sorting personnel. While the invention is preferred for use in sorting mail, those skilled in the art can appreciate that other objects or areas may be contained using the invention.

Figure 1:
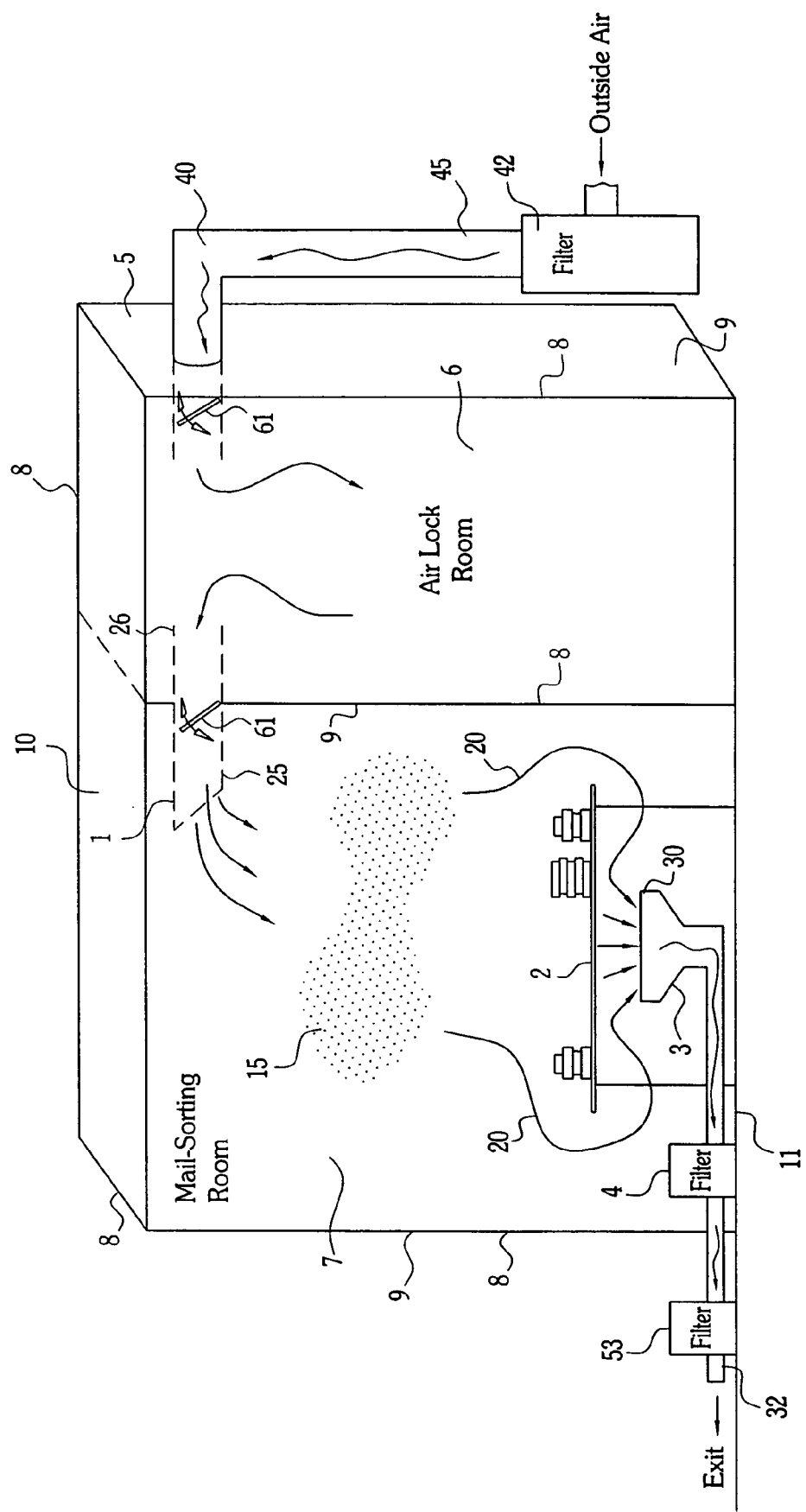
FIG. 1 is a diagram showing a preferred embodiment of the system of the present invention for removing contaminates from the air in a mail sorting room.
Figure 2:
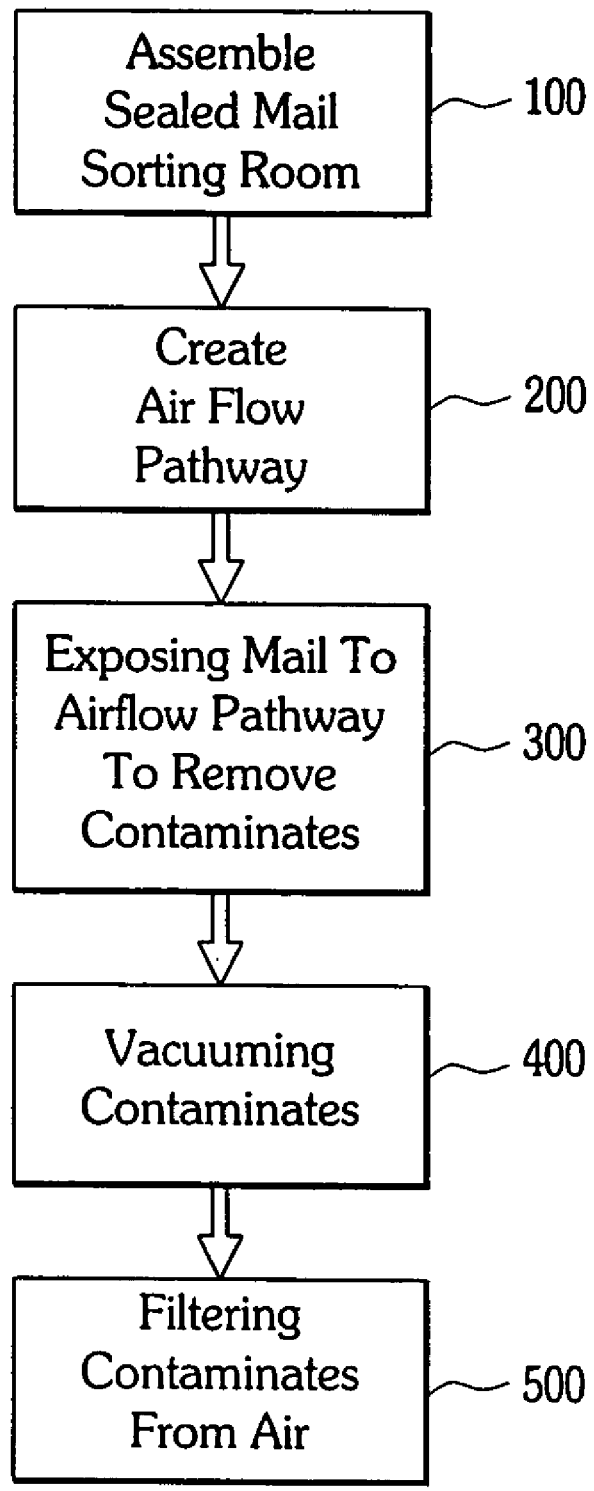
FIG. 2 is a diagram showing steps included in a preferred embodiment of the method of the present invention for removing contaminates from the air in a mail sorting room.

Referring to FIG. 1, a preferred embodiment of the system of the present invention includes an air inlet 1, a sorting table 2, a vacuum unit 3, and a filter unit 4. The sorting table is located within a sealed enclosure 5 which includes an air lock room 6 and a mail sorting room 7, the latter of which is large enough to accommodate at least one worker and a collection of mail. The sealed enclosure may have any shaped desired with a parallelopiped being preferable. The enclosure may also have a footprint which corresponds to other geometrical shapes (e.g., triangular, hexagonal, etc.) or may even be irregularly shaped. As will be explained below, one particularly advantageous feature of the invention is that the room may be designed to be portable with removable walls, floor, and ceiling. The dimensions of such a room are adapted to meet the space requirements given. For example, a media company may have set aside a certain limited amount of space in a mail room to accommodate the invention and the invention may be designed accordingly. The room may be a permanent room if desired.

To simplify installation, the room is preferably constructed to be modular in nature, fabricated from a frame comprising a plurality of interconnected support members 8. The support members may be made from any type of rigid material including metal, plastic, polymers, composites, and even wood. For convenience and ease of use, the members are made from a light but strong metal (e.g., aluminum) and are removably connected to allow the room to be portable and thus relocatable within, for example, an office building, warehouse, or the like.

The walls 9 of the room are made from plastics, polymers, composites, or any other material which is capable of enclosing a volume of air without leakage. In terms of appearance, the walls may be transparent, translucent, or even opaque for privacy reasons. Preferably, the walls are made from shatter-resistant Lexan which provides an easy-to-clean interior surface. In terms of structure, the walls may be rigid or flexible and a door or other entrance (not shown) is formed in one of the walls to allow personnel to pass into and out of the room. Like the walls, the door is sealed, or self-sealing, to prevent contaminates from escaping from the room.

The ceiling 10 of the room may be made from the same material as the walls. The floor 11 may be made from rubber, polymer, or a composite material which is not only airtight but which provides traction to sorting personnel while working in the room. The connections between the frame members, ceiling, and floor are all sealed using any one of a variety of conventional methods. As will become more apparent from the discussion which follows, sealing the room protects personnel outside the room from exposure to contaminates during mail sorting. Sealing the room also ensures that a sufficiently strong negative air-flow is created within the mail sorting room for cleaning the air therein.

The vacuum unit includes an air inlet 30 connected to a conduit 32 which exits the enclosure. The air inlet 30 may include a pre-filter which may be any standard heating and air filter. A mesh filter is one example. The conduit may exit the enclosure through the air lock room or through one of the walls in the mail sorting room. The air inlet is positioned under the table and suctions air from the mail sorting room as a result of a motorized blower (not shown) which may be located inside or outside of the enclosure. The blower (e.g., a thermally protected Class "B" insulated motor) may be located inside or outside the room. While the dimensions of the air inlet are shown as being smaller than the table, those skilled in the art can appreciate that the air inlet may be as large or even slightly larger than the table top.

The power of the vacuum unit is controlled to create a negative pressure within the mail sorting room. Preferably, the vacuum creates a negative pressure on the order of two atmospheres. (In this case, the vacuum unit may be said to create a double negative pressure environment.) To create such a negative pressure, the blower may create a suction on the order of 350-400 cubic feet per minute. Those skilled in the art can appreciate, however, that this range is merely illustrative and that other ranges may also be used.

The negative pressure in the sorting room draws airborne particulates 15 into the inlet of the vacuum unit and through the filter unit 4, after which it is expelled. The vacuum unit thus creates a constant flow of air directed towards the floor, which advantageously prevents the floating effect of airborne anthrax spores which have been found to infect workers in the latest terrorist attacks. This is especially effective in preventing infection through cross-contamination. (The air flow path created by the vacuum unit is preferably a laminar flow, as illustratively shown by arrows 20 in FIG. 1.)

The downward flow of air in the mail sorting room is created when the negative pressure created by the vacuum unit draws air through air inlet 1. As shown, this air inlet has a first end 25 which extends into the mail sorting room and a second end 26 which opens into the air lock room. In operation, negative pressure within the sorting room draws air from the air lock into the sorting room through air inlet 1. Air flows into the air lock room though another inlet 40, which has an end 45 attached to a filter unit 42. The air lock room includes at least two doors (not shown). The first door allows personnel to pass from the outside into the air lock room, and the second door passes from the air lock room into the mail sorting room. Inlets 1 and 40 may be equipped with internal valves 61 which close when negative pressure becomes reduced. These valves are advantageous because the prevent air in the mail-sorting room (which is potentially contaminated) from escaping into the air lock room or even outside of the entire enclosure. Like the mail sorting room, the air lock room may also be sealed.

The filter unit 4 may be any type conventionally known. Preferably, the filter unit includes dual-stage units which may be located inside or outside of the sealed room, or both. The filter units may also be included within a common housing with a motor of the vacuum unit. For example, the filter unit may be situated above the vacuum motor in unit 4. Under these circumstances, the vacuum motor and filter unit may be self-contained and disposable.

The first filter stage in unit 4 removes large particulates, for example, in the size range of above 5 microns. One filter of this type is a foam pre-filter. The second filter stage removes smaller particulates down to the size range of 0.3 microns. One filter of this type is a High Efficiency Particulate Air (HEPA) filter created by the U.S. Atomic Energy Commission. Such a filter has been shown to be 99.97% efficient at removing particles which are 0.3 microns in size or greater. HEPA filters of various sizes and materials may be used in accordance with the invention. Such a filter may have a netted structure of borosilicate fibers with 100 square feet of filter surface. The use of HEPA filters is advantageous not only for the aforementioned reasons but also because they tend to have a long operating life, e.g., 2-5 years. If desired, filter 42 may also be a HEPA filtration unit, or even a double HEPA unit. Once the air flow containing the contaminates has passed through filter unit 4, it may be expelled into the atmosphere, or it may be passed through another filter 53 which, for example, may also be a HEPA filter.

If desired, an optional third filter may be used to filter the air entering into the inlet of the vacuum unit. This third filter may be a V.O.C. filter which removes hazardous chemical threats. The third filter may be located at any position relative to the first two filter units, e.g., before them, after them, or even between them.

Referring to FIG. 2, a preferred embodiment of the method of the present invention includes as an initial step assembling an enclosure which includes mail sorting and air lock rooms as previously discussed. (Block 100). This involves selecting a location within, for example, an office building where an employer has dedicated space for mail to be sorted. The frame is then connected, followed by assembly of the walls, floor, and ceiling. If desired, the floor may be a rubber mat sealed to the underside of the frame and/or walls. The vacuum and filter units are then mounted, sealed to the room as necessary, and then powered. While the air lock room is considered advantageous in preventing contaminates from migrating from the mail sorting room to the outside environment, those skilled in the art can appreciate that only the mail sorting room may be constructed if desired.

A second step includes activating the vacuum unit to create a negative pressure within the mail sorting room. (Block 200). This causes air to be drawn first from the outside into the air lock room through conduit 40 and filter unit 42, and then from the air lock room into the mail sorting room through air inlet 1. As previously indicated, a negative pressure of two atmospheres is desirable for generating this air flow.

A third step includes placing an item of mail on the top surface of the table, or merely handling the mail item at a position above the table within the downwardly directed air flow pathway. In this position, any contaminates on the outside of the mail or suspended in the art are suctioned into the air inlet of the vacuum unit.(Block 300). To ensure that contaminates are removed, the mail handler should rotate the mail item so that all of its surfaces are subjected to the air flow for at least a minimum amount of time.

A fourth step includes allowing the suction created by the vacuum unit to carry the contaminates from the air in the mail sorting room into the inlet of the vacuum. (Block 400). Once in the inlet, the contaminates are carried to filter unit 4.

A fifth step includes filtering the air which has entered into the vacuum unit. (Block 500). This filtering step may be performed using one filter or multiple filters. Preferably, filtering is performed in at least two stages, where in a first stage larger sized particles are removed and in a second stage smaller size particles (e.g., 0.3 microns) are removed. A third filter stage may remove chemical threats that may exist in the air flow.

A number of optional features may be included in each of the foregoing embodiments. For example, multiple sorting rooms with separate air lock rooms or even a common air lock room may be used. These sorting rooms may be connected to a common frame structure but each may be isolated from the other for containment purposes. The rooms may be constructed such as shown in FIG. 1, complete with their own tables, vacuums, and filter units. For cost saving and convenience, a single air source for the blowers may be used in combination with a branched conduit. Also, the conduit on the air inlet of each vacuum unit may lead into a common filter unit. Doors (not shown) may be included not only to allow personnel to enter each room from the outside but also to allow personnel to pass between the rooms. As in the first embodiment, airtight seals are provided at all locations where the conduits and other structure of the system pass through the walls and/or ceiling.

In addition to a sorting table, a mail inspection table and/or one or more mail openers may be included in every sealed room. Each room may also contain sterilization equipment which may be used to sterilize a contaminated letter once found. Each room may also be equipped with a beacon or other warning/indication device which may be activated to alert exterior personnel that the room is in use. Each room may also include its own intercom system for communicating with persons outside the room.

Figure 3:
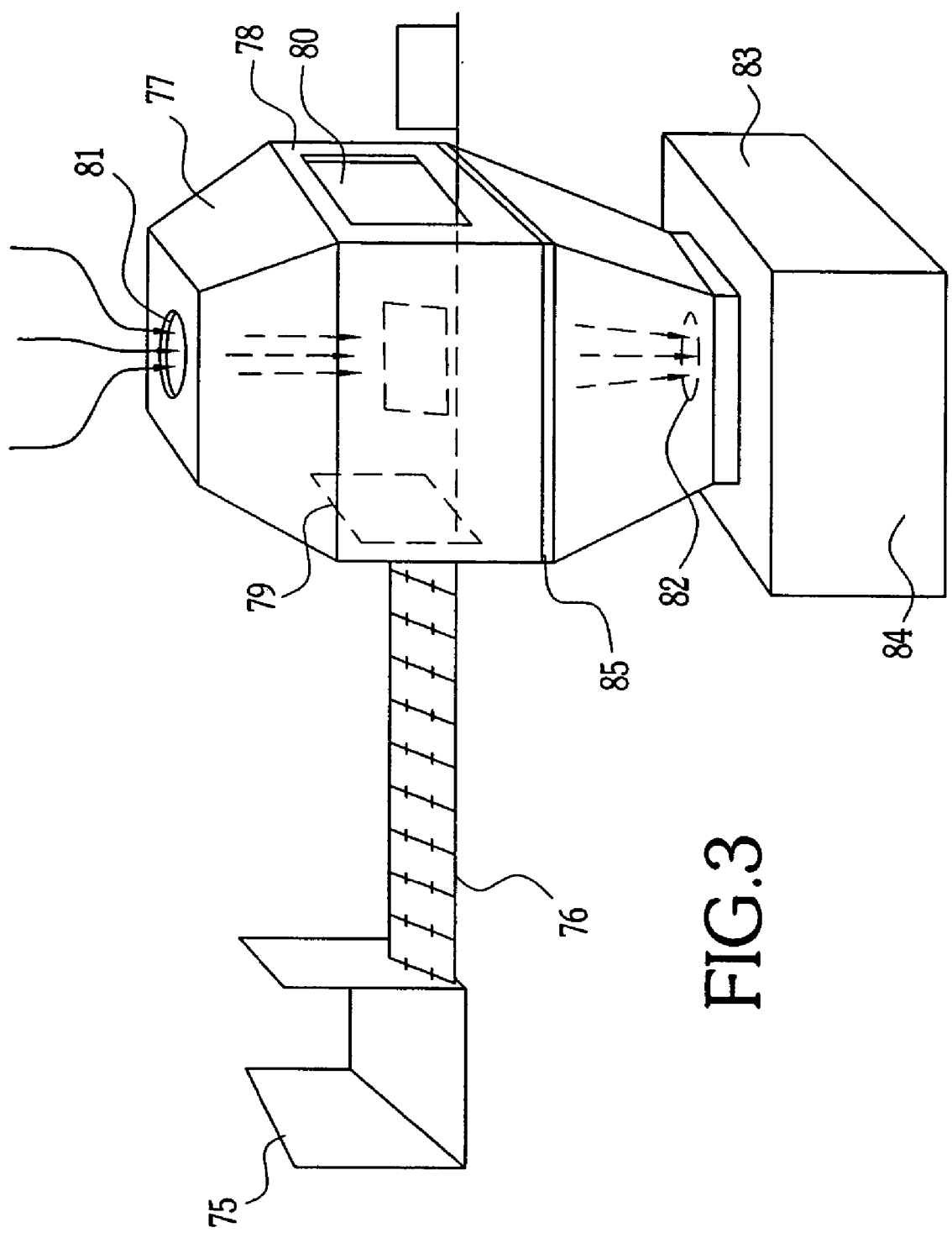
FIG. 3 is a diagram showing an embodiment of a mail cleaning device in accordance with the present invention which is suitable for use in the mail sorting room.

One optional feature which may be placed on or adjacent the sorting table is what the Inventor refers to as a high velocity, high CFM vacuum device. As shown in FIG. 3, this device may be connected to a self-feeding mail tray 75 via conveyor 76, which is designed to hold the mail on edge and move it rapidly to the device. The conveyor may shake the mail during transport utilizing existing technology. Rollers, wheels, tracks, or other known components may be incorporated into the conveyor for moving the mail. If desired, the conveyor may be motorized for automatically conveying the mail to the vacuum device.

The vacuum device 77 includes a chamber 78 having an entrance 79 and an exit 80 through which the mail passes from the conveyor. The vacuum device also includes an air intake port 81 and an air outlet port 82, the latter of which is attached to a motorized vacuum unit 83 which includes a filter 84 such as a HEPA filter. A pre-filter 85 may be integrated into the housing of the chamber in advance of HEPA filter 84.

In operation, a worker in the mail sorting room would fill the mail tray with a stack of mail. The conveyor would then transport the mail to the vacuum device. Inside the chamber of the vacuum device, a high-speed air flow is created as a result of vacuum unit 83 suctioning air through the air intake port. Preferably, the vacuum unit creates a down draft of air in the range of 50 to 400 C.F.M., but those skilled in the art can appreciate that other air flow ranges may just as easily be used. The air flow created within the chamber operates as an air wash to remove contaminates (e.g., anthrax spores, pollen, etc.) from the mail. If desired, the exhaust from the vacuum unit 83 may be ducted into a secondary filter to be re-filtered through a HEPA filter for redundant safety.

After the mail exits the vacuum chamber, it is passed either to a mail opener or stacked into a bundle for sorting. This may be accomplished by extending the conveyor through the chamber housing and exit along additional conveyor track connected to the exit, or simply by allowing the mail to drop into a bin situated below the exit. If the device is a desktop unit, the mail may be left to drop onto the sorting table. The vacuum device provides an additional measure of protection when used in combination with the mail sorting room of the present invention.

Other modifications and variations to the invention will be apparent to those skilled in the art from the foregoing disclosure. Thus, while only certain embodiments of the invention have been specifically described herein, it will be apparent that numerous modifications may be made thereto without departing from the spirit and scope of the invention.

I claim:

1. An air decontamination system, comprising
    a sealed room to hold at least one person and said sealed room having an air inlet;
    a vacuum unit to create a negative pressure within said sealed room, by suctioning air through the air inlet into said sealed room and then from said sealed room into an inlet of said vacuum unit;
    a work surface disposed in said sealed room at a predetermined height above a floor of said sealed room, said work surface to receive at least one mail piece, said air to be suctioned downwardly over said at least one mail piece and said work surface; and
    a filter unit to filter said air as said air is drawn out of the sealed room.

2. The air decontamination system of claim 1, wherein said sealed room has a modular construction.

3. The air decontamination system of claim 1, wherein said sealed room includes removable walls.

4. The air decontamination system of claim 3, wherein said sealed room includes at least one of a removable ceiling and a removable floor.

5. The air decontamination system of claim 3, wherein said sealed room includes a removable ceiling and a removable floor.

6. The air decontamination system of claim 1, wherein said sealed room has at least one transparent wall.

7. The air decontamination system of claim 1, further comprising:
    an air lock room connected to said sealed room,
    wherein said air inlet extends between said sealed room and said air lock room, and wherein the air suctioned through said air inlet resides within said air lock room.

8. The air decontamination system of claim 7, further comprising:
    another air inlet which allows air to pass from an outside source into said air lock room, wherein the negative pressure created by said vacuum unit draws air from said outside source into said sealed room through said another air inlet and said air inlet.

9. The air decontamination system of claim 8, further comprising:
    another filter unit connected to said another air inlet, said another filter unit filtering air from said outside source.

10. The air decontamination system of claim 1, further comprising:
    an intercom system which allows a person outside said sealed room to communicate with a person inside said sealed room.

11. The air decontamination system of claim 1, further comprising:
    a warning device which provides an indication that said sealed room is in use.

12. The air decontamination system of claim 1, wherein said vacuum unit creates a laminar flow of air within said sealed room.

13. The air decontamination system of claim 1, wherein said filter unit includes:
    a first filter which filters particles within a first range of sizes; and a second filter which filters particles within a second range of sizes,
    wherein said second range of sizes is smaller than said first range of sizes.

14. The air decontamination system of claim 13, wherein said filter unit includes a third filter which removes chemical contaminates.

15. The air decontamination system of claim 1, wherein said air is to be further suctioned downwardly over said at least one mail piece and through said work surface.

16. The air decontamination system of claim 15, further comprising:
    an air lock room connected to said sealed room, wherein said air inlet extends between said sealed room and said air lock room, and wherein the air suctioned through said air inlet resides within said air lock room.

17. The air decontamination system of claim 16, further comprising:

another air inlet which allows air to pass from an outside source into said air lock room, wherein the negative pressure created by said vacuum unit draws air from said outside source into said sealed room through said another air inlet and said air inlet.

18. The air decontamination system of claim 17, further comprising:
another filter unit connected to said another air inlet, said another filter unit filtering air from said outside source.

19. The air decontamination system of claim 15, wherein said filter unit includes:

a first filter which filters particles within a first range of sizes; and a second filter which filters particles within a second range of sizes, wherein said second range of sizes is smaller than said first range of sizes.

20. The air decontamination system of claim 19, wherein said filter unit includes a third filter which removes chemical contaminates.

\* \* \* \* \*